(12) United States Patent
Laughner et al.

(10) Patent No.: US 9,763,625 B2
(45) Date of Patent: Sep. 19, 2017

(54) MEDICAL DEVICES FOR MAPPING CARDIAC TISSUE

(71) Applicant: BOSTON SCIENTIFIC SCIMED, INC., Maple Grove, MN (US)

(72) Inventors: Jacob I. Laughner, St. Paul, MN (US); Shibaji Shome, Arden Hills, MN (US); Pramodsingh Hirasingh Thakur, Woodbury, MN (US); Scott A. Meyer, Lakeville, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 14/705,395

(22) Filed: May 6, 2015

(65) Prior Publication Data

US 2016/0007932 A1 Jan. 14, 2016

Related U.S. Application Data

(60) Provisional application No. 61/991,235, filed on May 9, 2014.

(51) Int. Cl.
*A61B 5/04* (2006.01)
*A61B 5/00* (2006.01)
(Continued)

(52) U.S. Cl.
CPC ............ *A61B 5/7257* (2013.01); *A61B 5/044* (2013.01); *A61B 5/0422* (2013.01);
(Continued)

(58) Field of Classification Search
CPC ...... A61B 18/1492; A61B 2018/00577; A61B 5/04014; A61B 5/0422; A61B 5/044;
(Continued)

(56) References Cited

U.S. PATENT DOCUMENTS 5,772,604 A 6/1998 Langberg et al.
5,795,304 A 8/1998 Sun et al.
(Continued)

FOREIGN PATENT DOCUMENTS

WO 9834540 A1 8/1998
WO WO0182099 A1 11/2001
(Continued)

OTHER PUBLICATIONS

Barquero-Perez, Oscar. Fundamental Frequency and Regularity of Cardiac Electrograms With Fourier Organization Analysis. IEEE Transactions on Biomedical Engineering, 57(9): 2168-2177, Sep. 2010.
(Continued)

*Primary Examiner* — Lindsey G Wehrheim
(74) *Attorney, Agent, or Firm* — Faegre Baker Daniels LLP

(57) ABSTRACT

Medical devices and methods for making and using medical devices are disclosed. An example method may include a method of mapping the electrical activity of a heart. The method may include sensing a plurality of signals with a plurality of electrodes positioned within the heart, determining a dominant frequency of the plurality of signals and generating an alternate signal for each of the plurality of signals corresponding to the dominant frequency. The alternate signals may have a phase-shift corresponding to one of the plurality of signals. The method may also include displaying a characteristic of the alternate signal over time.

16 Claims, 11 Drawing Sheets

(51) Int. Cl.
*A61B 5/042* (2006.01)
*A61B 5/044* (2006.01)
*A61B 18/14* (2006.01)
*A61B 18/00* (2006.01)

(52) U.S. Cl.
CPC ............ *A61B 5/6858* (2013.01); *A61B 5/725* (2013.01); *A61B 5/7253* (2013.01); *A61B 5/7278* (2013.01); *A61B 18/1492* (2013.01); *A61B 5/04014* (2013.01); *A61B 2018/00577* (2013.01)

(58) Field of Classification Search
CPC ..... A61B 5/6858; A61B 5/725; A61B 5/7253; A61B 5/7257; A61B 5/7278
See application file for complete search history.

(56) References Cited

U.S. PATENT DOCUMENTS

| | | | |
|---|---|---|---|
| 6,070,094 | A | 5/2000 | Swanson et al. |
| 6,233,491 | B1 | 5/2001 | Kordis et al. |
| 6,293,915 | B1 | 9/2001 | Amano et al. |
| 6,735,465 | B2 | 5/2004 | Panescu |
| 7,376,458 | B2 | 5/2008 | Palreddy et al. |
| 7,751,873 | B2 | 7/2010 | de Voir |
| 8,010,186 | B1 | 8/2011 | Ryu |
| 8,543,195 | B1 | 9/2013 | Brockway et al. |
| 9,408,544 | B2 | 8/2016 | Laughner et al. |
| 2004/0059237 | A1 | 3/2004 | Narayan et al. |
| 2004/0176696 | A1 | 9/2004 | Mortara |
| 2007/0299351 | A1 | 12/2007 | Harlev et al. |
| 2009/0143692 | A1 | 6/2009 | Brockway et al. |
| 2010/0014723 | A1 | 1/2010 | Addison et al. |
| 2010/0016693 | A1 | 1/2010 | Addison et al. |
| 2012/0184863 | A1 | 7/2012 | Harlev et al. |
| 2012/0232417 | A1 | 9/2012 | Zhang |
| 2013/0006131 | A1 | 1/2013 | Narayan et al. |
| 2013/0279881 | A1 | 10/2013 | Lu et al. |
| 2014/0051961 | A1 | 2/2014 | Badower et al. |
| 2014/0088395 | A1 | 3/2014 | Dubois et al. |
| 2014/0200467 | A1 | 7/2014 | Strom et al. |
| 2014/0330145 | A1 | 11/2014 | Brodnick |
| 2015/0342488 | A1 | 12/2015 | Laughner et al. |

FOREIGN PATENT DOCUMENTS

| | | |
|---|---|---|
| WO | 2005115232 A1 | 12/2005 |
| WO | WO2006037172 A1 | 4/2006 |
| WO | 2006060366 A2 | 6/2006 |
| WO | 2007137045 A2 | 11/2007 |
| WO | 2008035070 A2 | 3/2008 |
| WO | 2010054409 A1 | 5/2010 |
| WO | 2011098944 A1 | 8/2011 |
| WO | 2012044261 A1 | 4/2012 |
| WO | WO2012151301 A1 | 11/2012 |
| WO | 2015171742 A1 | 11/2015 |
| WO | 2015171898 A1 | 11/2015 |

OTHER PUBLICATIONS

Citi, et. al. A Real-Time Automated Point Process Method for Detection and Correction of Erroneous and Ectopic Heartbeats. IEEE Trans. Biomed. Eng., 59(10): 2828-2837, Oct. 2012.
International Search Report and Written Opinion issued in PCT/US2015/029697, mailed Jul. 14, 2015, 13 pages.
Tateno, et, al. Automatic Detection of Atrial Fibrillation Using the Coefficient of Variation and Density Histograms of RR and DeltaRR Intervals. Med, Biol. Eng. Comput., 39:664-671, 2001.
International Search Report and Written Opinion issued in PCT/U52015/029441, mailed Jul. 23, 2015, 12 pages.
Ahmad, A., et al. Evolution of Frequency of Composition for Atrial Arrhythmias. Jurnal Teknologi (Sciences & Engineering) 69(8):27-29, 2014.
Ciaccio, Edward J. et al: A new transform for the analysis of complex fractinated atrial electrograms:, BioMedical Engineering Online, Biomed Central Ltd, London, GB, vol. 10, No. 1, May 12, 2011, pp. 1-27.
Ciaccio, Edward J., et al. New Methods for Estimating Local Electrical Activation Rate During Atrial Fibrillation. Heart Rhythm 6:21-32, 2009.
International Preliminary Report on Patentability issued in PCT/US2015/029441, mailed Nov. 15, 2016, 9 pages.
International Search Report and Written Opinion issued in PCT/US2015/053747, mailed Jan. 5, 2016, 11 pages.
International Search Report and Written Opinion issued in PCT/US2015/053831, mailed Jan. 7, 2016, 15 pages.
International Search Report and Written Opinion issued in PCT/US2015/053842, mailed Dec. 17, 2015, 10 pages.
Minh Phuong Nguyen et al: "A new approach for frequency analysis of complex fractionated atrial electrograms", Proceedings of the 31st Annual international Conference of the IEEE Engineering in Medicine and Biology Society: Engineering the Future of Biomedicine, EMBC 2009, IEEE, Sep. 3, 2009, pp. 368-371.
Monzon, Sandra et al: "Sparse spectral analysis of atrial fibrillation electrograms", 2012 IEEE International Workshop on Machine Learning for Signal Processing, Sep. 23, 2012, pp. 1-6.
Riccio, Mark L., et al. Electrical Restitution and Spatiotemporal Organization During Ventricular Fibrillation. Circ Res., 84:955-963.
Swissa, Moshe, et al. Action Potential Duration Restitution and Ventricular Fibrillation Due to Rapid Focal Excitation. American Journal of Physiology—Heart and Circulatory Physiology, 282:H1915-H1923, 2002.

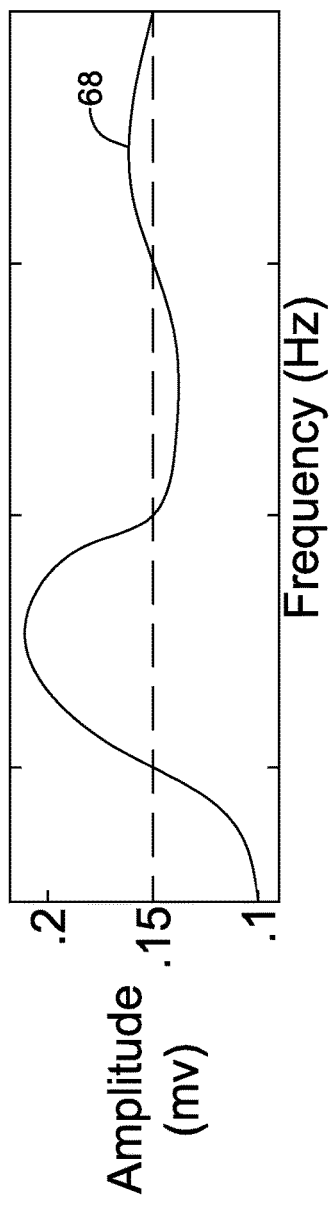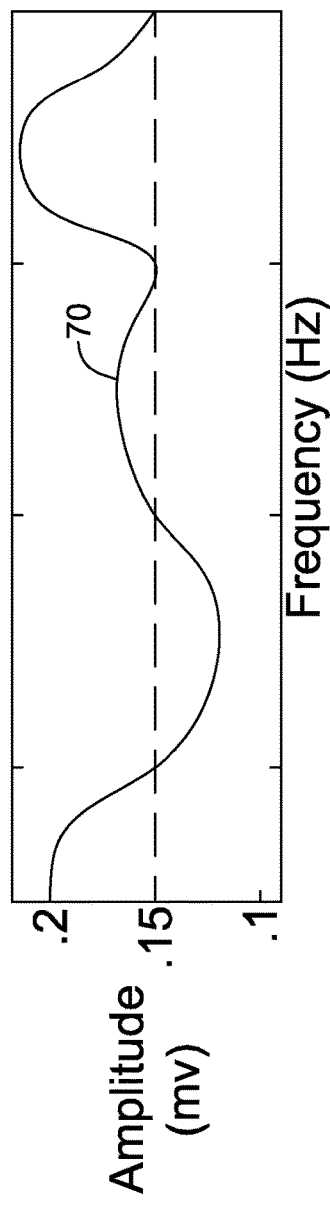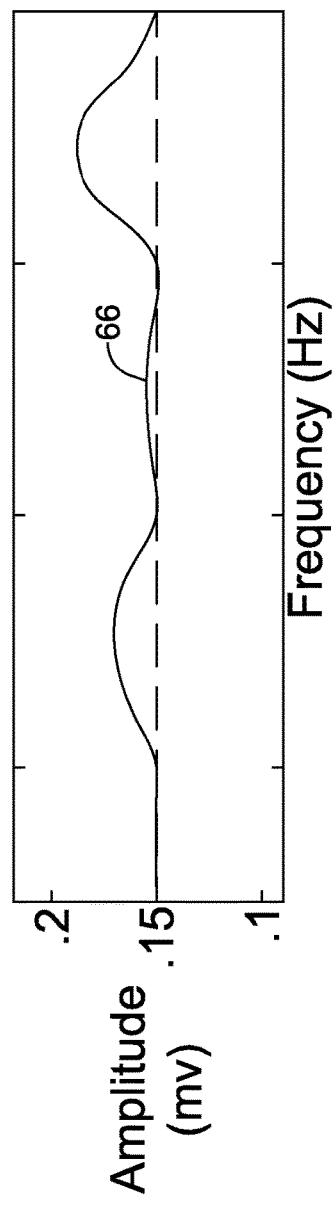

MEDICAL DEVICES FOR MAPPING CARDIAC TISSUE

CROSS-REFERENCE TO RELATED APPLICATIONS

This application claims priority under 35 U.S.C. §119 to U.S. Provisional Application Ser. No. 61/991,235, filed May 9, 2014, the entirety of which is incorporated herein by reference.

TECHNICAL FIELD

The present disclosure pertains to medical devices, and methods for manufacturing medical devices. More particularly, the present disclosure pertains to medical devices and methods for mapping and/or ablating cardiac tissue.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices.

In a first example, a system for mapping the electrical activity of the heart is disclosed. The system includes a catheter shaft, a plurality of electrodes coupled to the catheter shaft and a processor coupled to the catheter shaft. The processor is configured to collect a plurality of signals sensed by the plurality of electrodes, determine a dominant frequency of the plurality of signals and generate an alternate signal for each of the plurality of signals corresponding to the dominant frequency. Further each of the alternate signals has a phase-shift corresponding to one of the plurality of signals. The processor may also display a characteristic of the alternate signal over time.

In addition or alternatively to the above, and in another example determining a dominant frequency includes processing each of the plurality of signals using a Fourier Transform, generating a composite signal based on the processed plurality of signals and identifying the frequency with the maximum power in the composite signal.

In addition or alternatively to any one or more of the above, and in another example the system includes band-pass filtering each of the processed plurality of signals.

In addition or alternatively to any one or more of the above, and in another example band-pass filtering includes passing data in the 3 to 7 Hz band for each of the processed plurality of signals.

In addition or alternatively to any one or more of the above, and in another example generating a composite signal based on the processed plurality of signals includes generating a composite signal with a value at each frequency that is one of a median value, a mean value, or a mode value of the processed plurality of signals at each frequency.

In addition or alternatively to any one or more of the above, and in another example the phase-shift of the alternate signal is based on the composite signal.

In addition or alternatively to any one or more of the above, and in another example each alternate signal is a sinusoid.

In addition or alternatively to any one or more of the above, and in another example each alternate signal is an analytic representation of a sinusoid.

In addition or alternatively to any one or more of the above, and in another example the analytic representation is generated by a Hilbert transform.

In addition or alternatively to any one or more of the above, and in another example the analytic representation is a sawtooth.

In addition or alternatively to any one or more of the above, and in another example the system includes determining a fiducial point on each alternate signal. Further, the fiducial point on each alternate signal is one of the following: a point with a maximum negative derivative, a point of zero-crossing, and a point at phase $\pi/2$.

In addition or alternatively to any one or more of the above, and in another example the system includes determining an activation time for each of the plurality of signals based on the identified fiducial points, generating an activation map based on the determined activation times for each of the plurality of signals, and displaying the activation map.

In addition or alternatively to any one or more of the above, and in another example displaying a characteristic of the alternate signal over time includes displaying a dynamic map.

In addition or alternatively to any one or more of the above, and in another example displaying a characteristic of the alternate signal over time includes displaying one or more phase values of one or more alternate signals.

In addition or alternatively to any one or more of the above, and in another example displaying a characteristic of the alternate signal over time includes displaying the results of the Hilbert transform on a dynamic map.

In addition or alternatively to any one or more of the above, and in another example a method of mapping the electrical activity of a heart is disclosed. The method includes sensing a plurality of signals with a plurality of electrodes positioned within the heart, determining a dominant frequency of the plurality of signals and generating an alternate signal for each of the plurality of signals corresponding to the dominant frequency. The alternate signals can have a phase-shift corresponding to one of the plurality of signals. The method can also include displaying a characteristic of the alternate signal over time.

In addition or alternatively to any one or more of the above, and in another example determining a dominant frequency includes processing each of the plurality of signals using a Fourier Transform, generating a composite signal based on the processed plurality of signals, and identifying the frequency with the maximum power in the composite signal.

In addition or alternatively to any one or more of the above, and in another example the method of mapping the electrical activity of a heart includes band-pass filtering each of the processed plurality of signals.

In addition or alternatively to any one or more of the above, and in another example band-pass filtering includes passing data in the 3 to 7 Hz band for each of the processed plurality of signals.

In addition or alternatively to any one or more of the above, and in another example generating a composite signal based on the processed plurality of signals includes generating a composite signal with a value at each frequency that is one of a median value, a mean value, or a mode value of the processed plurality of signals at each frequency.

In addition or alternatively to any one or more of the above, and in another example the phase-shift of the alternate signal is based on the composite signal.

In addition or alternatively to any one or more of the above, and in another example each alternate signal is a sinusoid.

In addition or alternatively to any one or more of the above, and in another example each alternate signal is an analytic representation of a sinusoid.

In addition or alternatively to any one or more of the above, and in another example the analytic representation is generated by a Hilbert transform.

In addition or alternatively to any one or more of the above, and in another example the analytic representation is a sawtooth.

In addition or alternatively to any one or more of the above, and in another example the fiducial point on each alternate signal is one of the following: a point with a maximum negative derivative, a point of zero-crossing, and a point at phase $\pi/2$.

In addition or alternatively to any one or more of the above, and in another example the method includes determining an activation time for each of the plurality of signals based on the identified fiducial points, generating an activation map based on the determined activation times for each of the plurality of signals, and displaying the activation map.

In addition or alternatively to any one or more of the above, and in another example a method for determining activation times in cardiac electrical signals is disclosed. The method includes sensing a plurality of cardiac electrical signals with a plurality of electrodes positioned within the heart and processing the plurality of signals. Processing the plurality of signals can include transforming the plurality of signals into the frequency domain. The method can also include generating a composite signal from the processed plurality of signals, identifying the largest frequency component from the composite signal, determining a phase value for each of the plurality of signals at the identified frequency and generating an approximation signal for each of the plurality of signals. The generated approximation signal can have a phase-shift. The method can also display a characteristic of the approximation signal over time.

In addition or alternatively to any one or more of the above, and in another example processing the plurality of signals includes removing data outside of the 3 to 7 Hz band in each of the plurality of signals.

In addition or alternatively to any one or more of the above, and in another example generating the composite signal from the processed plurality of signals includes determining the median value of all of the plurality of signals at each frequency, determining the mean value of all of the plurality of signals at each frequency, or determining the mode value of all of the plurality of signals at each frequency.

In addition or alternatively to any one or more of the above, and in another example the method includes determining a fiducial point on each approximation signal, determining an activation time for each of the plurality of signals based on the identified fiducial points, generating an activation map based on the determined activation times for each of the plurality of signals, and displaying the activation map.

In addition or alternatively to any one or more of the above, and in another example a system for mapping the electrical activity of the heart is disclosed. The system includes a catheter shaft, a plurality of electrodes coupled to the catheter shaft and a processor coupled to the catheter shaft. The processor can be configured to collect a plurality of signals sensed by the plurality of electrodes, determine a dominant frequency of the plurality of signals and generate an alternate signal for each of the plurality of signals corresponding to the dominant frequency. The alternate signals can have a phase-shift corresponding to one of the plurality of signals. The system can also include displaying a characteristic of the alternate signals over time.

In addition or alternatively to any one or more of the above, and in another example to determine a dominant frequency of the plurality of signals, the processor is further configured to transform each of the plurality of signals into the frequency domain, generate a composite signal from each of the transformed plurality of signals and determine the frequency that has the maximum power in the composite signal.

In addition or alternatively to any one or more of the above, and in another example each alternate signal is a sinusoid or a sawtooth.

In addition or alternatively to any one or more of the above, and in another example each alternate signal is an analytic representation of a sinusoid.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIGS. 5A-5C are illustrations of example frequency spectrums and a corresponding composite frequency spectrum;

Figure 1:
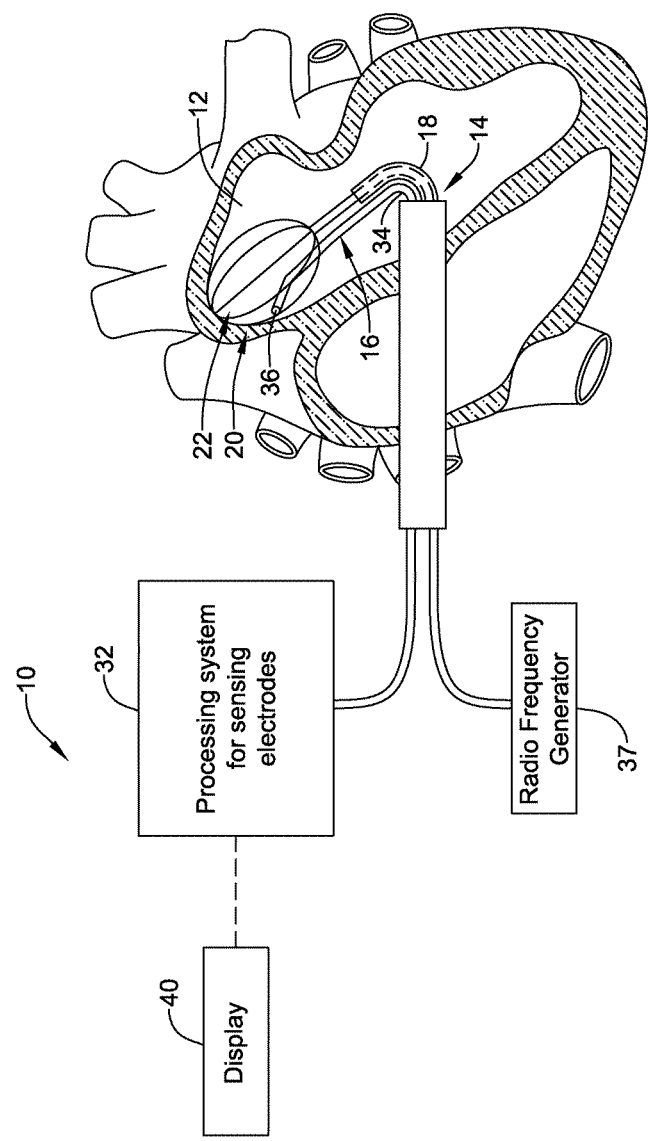
FIG. 1 is a schematic view of an example catheter system for accessing a targeted tissue region in the body for diagnostic and therapeutic purposes.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an example", "some examples", "other examples", etc., indicate that the example described may include one or more particular features, structures, and/or characteristics. However, such recitations do not necessarily mean that all examples include the particular features, structures, and/or characteristics. Additionally, when particular features, structures, and/or characteristics are described in connection with one example, it should be understood that such features, structures, and/or characteristics may also be used connection with other examples whether or not explicitly described unless clearly stated to the contrary. Also, when particular features, structures, and/or characteristics are described in connection with one example, it is implicit that other examples may include less than all of the disclosed features, structures, and/or characteristics in all combinations.

The following detailed description should be read with reference to the drawings in which similar elements in different drawings are numbered the same. The drawings, which are not necessarily to scale, depict illustrative embodiments and are not intended to limit the scope of the invention.

Mapping the electrophysiology of heart rhythm disorders often involves the introduction of a basket catheter (e.g. Constellation) or other mapping/sensing device having a plurality of sensors into a cardiac chamber. The sensors, for example electrodes, detect physiological signals, such as cardiac electrical activity, at sensor locations. It may be desirable to have detected cardiac electrical activity processed into electrogram signals that accurately represent cellular excitation through cardiac tissue relative to the sensor locations. A processing system may then analyze and output the signal to a display device. Further, the processing system may output the signal as processed output, such as a static or dynamic activation map. A user, such as a physician, may use the processed output to perform a diagnostic procedure.

FIG. 1 is a schematic view of a system 10 for accessing a targeted tissue region in the body for diagnostic and/or therapeutic purposes. FIG. 1 generally shows the system 10 deployed in the left atrium of the heart. Alternatively, system 10 can be deployed in other regions of the heart, such as the left ventricle, right atrium, or right ventricle. While the illustrated embodiment shows system 10 being used for ablating myocardial tissue, system 10 (and the methods described herein) may alternatively be configured for use in other tissue ablation applications, such as procedures for ablating tissue in the prostrate, brain, gall bladder, uterus, nerves, blood vessels and other regions of the body, including in systems that are not necessarily catheter-based.

System 10 includes a mapping catheter or probe 14 and an ablation catheter or probe 16. Each probe 14/16 may be separately introduced into the selected heart region 12 through a vein or artery (e.g., the femoral vein or artery) using a suitable percutaneous access technique. Alternatively, mapping probe 14 and ablation probe 16 can be assembled in an integrated structure for simultaneous introduction and deployment in the heart region 12.

Mapping probe 14 may include flexible catheter body 18. The distal end of catheter body 18 carries three-dimensional multiple electrode structure 20. In the illustrated embodiment, structure 20 takes the form of a basket defining an open interior space 22 (see FIG. 2), although other multiple electrode structures could be used. Structure 20 carries a plurality of mapping electrodes 24 (not explicitly shown on FIG. 1, but shown on FIG. 2) each having an electrode location on structure 20 and a conductive member. Each electrode 24 may be configured to sense or detect intrinsic physiological activity, for example represented as electrical signals, in an anatomical region adjacent to each electrode 24.

In addition, electrodes 24 may be configured to detect activation signals of the intrinsic physiological activity within the anatomical structure. For example, intrinsic cardiac electrical activity may comprise repeating or semi-repeating waves of electrical activity with relatively large spikes in activity at the beginning of activation events. Electrodes 24 may sense such activation events and the times at which such activation events occur. Generally, electrodes 24 may sense activation events at different times as an electrical activity wave propagates through the heart. For instance, an electrical wave may begin near a first group of electrodes 24, which may sense an activation event at relatively the same time or within a relatively small window of time. As the electrical wave propagates through the heart, a second group of electrodes 24 may sense the activation event of the electrical wave at times later than the first group of electrodes 24.

Electrodes 24 are electrically coupled to processing system 32. A signal wire (not shown) may be electrically coupled to each electrode 24 on structure 20. The signal wires may extend through body 18 of probe 14 and electrically couple each electrode 24 to an input of processing system 32. Electrodes 24 sense cardiac electrical activity in the anatomical region, e.g., myocardial tissue, adjacent to their physical location within the heart. The sensed cardiac electrical activity (e.g., electrical signals generated by the heart which may include activation signals) may be processed by processing system 32 to assist a user, for example a physician, by generating processed output—e.g. an anatomical map (e.g., a vector field map, an activation time map) or a Hilbert transform diagram—to identify one or more sites within the heart appropriate for a diagnostic and/or treatment procedure, such as an ablation procedure.

For example, processing system 32 may identify a near-field signal component (e.g., activation signals originating from cellular tissue adjacent to mapping electrodes 24) or an obstructive far-field signal component (e.g., activation signals originating from non-adjacent tissue). In such examples where structure 20 is disposed in an atrium of the heart, as in FIG. 1, the near-field signal component may include activation signals originating from atrial myocardial tissue whereas the far-field signal component may include activation signals originating from ventricular myocardial tissue. The near-field activation signal component may be further analyzed to find the presence of a pathology and to determine a location suitable for ablation for treatment of the pathology (e.g., ablation therapy).

Processing system 32 may include dedicated circuitry (e.g., discrete logic elements and one or more microcontrollers; application-specific integrated circuits (ASICs); or specially configured programmable devices, such as, for example, programmable logic devices (PLDs) or field programmable gate arrays (FPGAs)) for receiving and/or processing the acquired physiological activity. In some examples, processing system 32 includes a general purpose microprocessor and/or a specialized microprocessor (e.g., a digital signal processor, or DSP, which may be optimized for processing activation signals) that executes instructions to receive, analyze and display information associated with the received physiological activity. In such examples, processing system 32 can include program instructions, which when executed, perform part of the signal processing. Program instructions can include, for example, firmware, microcode or application code that is executed by microprocessors or microcontrollers. The above-mentioned implementations are merely exemplary, and the reader will appreciate that processing system 32 can take any suitable form for receiving electrical signals and processing the received electrical signals.

In addition, processing system 32 may be configured to measure the sensed cardiac electrical activity in the myocardial tissue adjacent to electrodes 24. For example, processing system 32 may be configured to detect cardiac electrical activity associated with a dominant rotor or divergent activation pattern in the anatomical feature being mapped. Dominant rotors and/or divergent activation patterns may have a role in the initiation and maintenance of atrial fibrillation, and ablation of the rotor path, rotor core, and/or divergent foci may be effective in terminating the atrial fibrillation. Processing system 32 processes the sensed cardiac electrical activity to generate a display of relevant characteristics. Such processed output may include isochronal maps, activation time maps, action potential duration (APD) maps, Hilbert transform diagrams, vector field maps, contour maps, reliability maps, electrograms, cardiac action potentials and the like. The relevant characteristics may assist a user to identify a site suitable for ablation therapy.

Ablation probe 16 includes flexible catheter body 34 that carries one or more ablation electrodes 36. The one or more ablation electrodes 36 are electrically connected to radio frequency (RF) generator 37 that is configured to deliver ablation energy to the one or more ablation electrodes 36. Ablation probe 16 may be movable with respect to the anatomical feature to be treated, as well as structure 20. Ablation probe 16 may be positionable between or adjacent to electrodes 24 of structure 20 as the one or more ablation electrodes 36 are positioned with respect to the tissue to be treated.

Processing system 32 may output data to a suitable device, for example display device 40, which may display relevant information for a user. In some examples, device 40 is a CRT, LED, or other type of display, or a printer. Device 40 presents the relevant characteristics in a format useful to the user. In addition, processing system 32 may generate position-identifying output for display on device 40 that aids the user in guiding ablation electrode(s) 36 into contact with tissue at the site identified for ablation.

Figure 2:
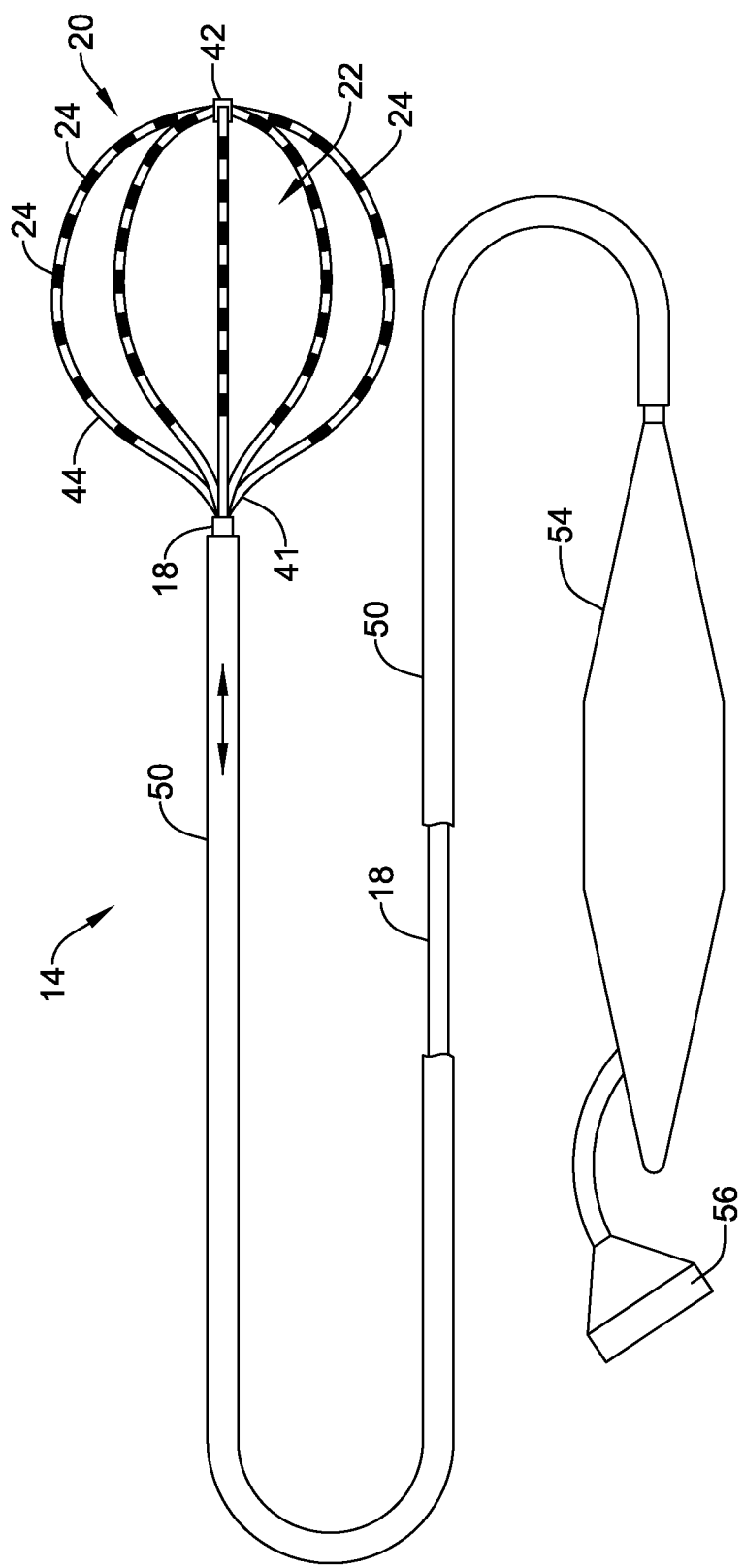
FIG. 2 is a schematic view of an example mapping catheter having a basket functional element carrying structure for use in association with the system of FIG. 1.

FIG. 2 illustrates mapping catheter 14 and shows electrodes 24 at the distal end suitable for use in system 10 shown in FIG. 1. Mapping catheter 14 may include flexible catheter body 18, the distal end of which may carry three-dimensional multiple electrode structure 20 with mapping electrodes or sensors 24. Mapping electrodes 24 may sense cardiac electrical activity, including activation signals, in the myocardial tissue. The sensed cardiac electrical activity may be processed by the processing system 32 to assist a user in identifying the site or sites having a heart rhythm disorder or other myocardial pathology via generated and displayed relevant characteristics. This information can then be used to determine an appropriate location for applying appropriate therapy, such as ablation, to the identified sites, and to navigate the one or more ablation electrodes 36 to the identified sites.

The illustrated three-dimensional multiple electrode structure 20 comprises base member 41 and end cap 42 between which flexible splines 44 generally extend in a circumferentially spaced relationship. As discussed herein, structure 20 may take the form of a basket defining an open interior space 22. In some examples, the splines 44 are made of a resilient inert material, such as Nitinol, other metals, silicone rubber, suitable polymers, or the like and are connected between base member 41 and end cap 42 in a resilient, pretensioned condition, to bend and conform to the tissue surface they contact. In the example illustrated in FIG. 2, eight splines 44 form three dimensional multiple electrode structure 20. Additional or fewer splines 44 could be used in other examples. As illustrated, each spline 44 carries eight mapping electrodes 24. Additional or fewer mapping electrodes 24 could be disposed on each spline 44 in other examples of three dimensional multiple electrode structure 20. In the example illustrated in FIG. 2, structure 20 is relatively small (e.g., 40 mm or less in diameter). In alternative examples, structure 20 is even smaller or larger (e.g., less than or greater than 40 mm in diameter).

Slidable sheath 50 may be movable along the major axis of catheter body 18. Moving sheath 50 distally relative to catheter body 18 may cause sheath 50 to move over structure 20, thereby collapsing structure 20 into a compact, low profile condition suitable for introduction into and/or removal from an interior space of an anatomical structure, such as, for example, the heart. In contrast, moving sheath 50 proximally relative to the catheter body may expose structure 20, allowing structure 20 to elastically expand and assume the pretensioned position illustrated in FIG. 2.

A signal wire (not shown) may be electrically coupled to each mapping electrode 24. The signal wires may extend through body 18 of mapping catheter 20 (or otherwise through and/or along body 18) into handle 54, in which they are coupled to external connector 56, which may be a multiple pin connector. Connector 56 electrically couples mapping electrodes 24 to processing system 32. It should be understood that these descriptions are just examples. Some addition details regarding these and other example mapping systems and methods for processing signals generated by a mapping catheter can be found in U.S. Pat. Nos. 6,070,094, 6,233,491, and 6,735,465, the disclosures of which are hereby expressly incorporated herein by reference.

Figure 3:
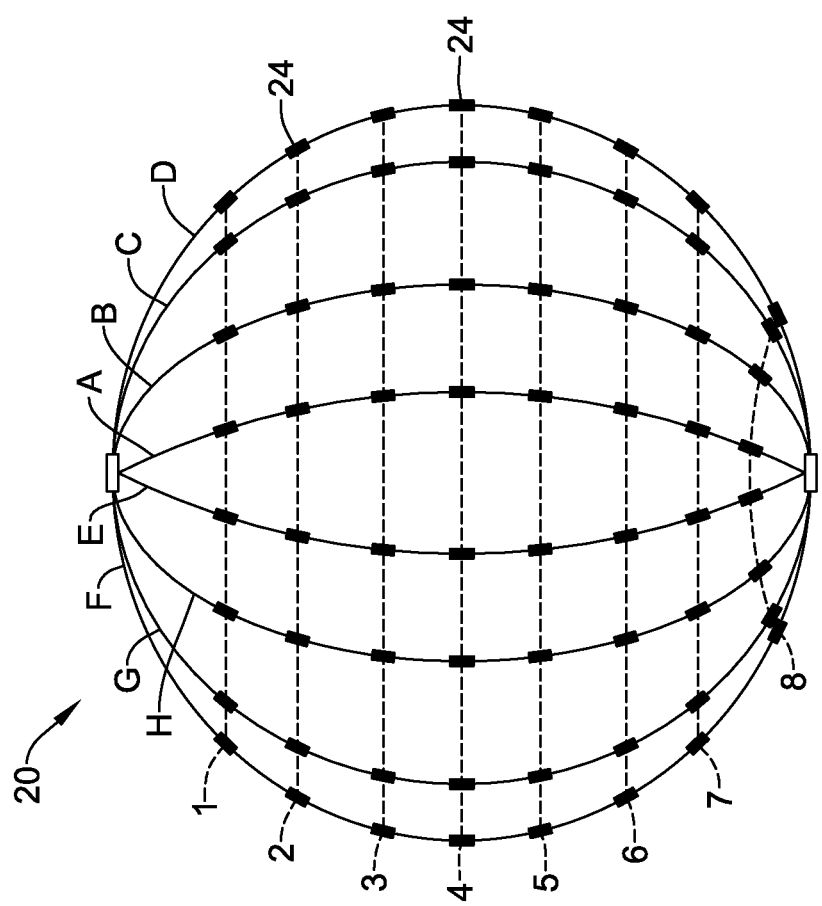
FIG. 3 is a schematic view of an example functional element including a plurality of mapping electrodes.

To illustrate the operation of system 10, FIG. 3 is a schematic side view of an example of basket structure 20 including a plurality of mapping electrodes 24. In the illustrated example, the basket structure includes 64 mapping electrodes 24. Mapping electrodes 24 are disposed in groups of eight electrodes (labeled 1, 2, 3, 4, 5, 6, 7, and 8) on each of eight splines (labeled A, B, C, D, E, F, G, and H). While an arrangement of sixty-four mapping electrodes 24 is shown disposed on basket structure 20, mapping electrodes 24 may alternatively be arranged in different numbers (more or fewer splines and/or electrodes), on different structures, and/or in different positions. In addition, multiple basket structures can be deployed in the same or different anatomical structures to simultaneously obtain signals from different anatomical structures.

After basket structure 20 is positioned adjacent to the anatomical structure to be treated (e.g. left atrium, left ventricle, right atrium, or right ventricle of the heart), processing system 32 is configured to record the cardiac electrical activity from each electrode 24 channel, and the cardiac electrical activity is related to physiological activity of the adjacent anatomical structure. For instance, cardiac electrical activity may include activation signals which may indicate an onset of physiological activity, such as a contraction of the heart. Electrodes 24 sense such cardiac electrical activity which includes activation signals. The cardiac electrical activity of physiological activity may be sensed in response to intrinsic physiological activity (e.g. intrinsically generated electrical signals) or based on a predetermined pacing protocol instituted by at least one of the plurality of electrodes 24 (e.g. delivered electrical signals delivered by a pacing device).

The arrangement, size, spacing and location of electrodes along a constellation catheter or other mapping/sensing device, in combination with the specific geometry of the targeted anatomical structure, may contribute to the ability (or inability) of electrodes 24 to sense, measure, collect and transmit electrical activity of cellular tissue. As stated, because splines 44 of a mapping catheter, constellation catheter or other similar sensing device are bendable, they may conform to a specific anatomical region in a variety of shapes and/or configurations. Further, at any given position in the anatomical region, structure 20 may be manipulated such that one or more splines 44 may not contact adjacent cellular tissue. For example, splines 44 may twist, bend, or lie atop one another, thereby separating splines 44 from nearby cellular tissue. Additionally, because electrodes 24 are disposed on one or more of splines 44, they also may not maintain contact with adjacent cellular tissue. Electrodes 24 that do not maintain contact with cellular tissue may be incapable of sensing, detecting, measuring, collecting and/or transmitting electrical activity information. Further, because electrodes 24 may be incapable of sensing, detecting, measuring, collecting and/or transmitting electrical activity information, processing system 32 may be incapable of accurately displaying diagnostic information and/or processed output. For example, some necessary information may be missing and/or displayed inaccurately.

In addition to that stated above, electrodes 24 may not be in contact with adjacent cellular tissue for other reasons. For example, manipulation of mapping catheter 14 may result in movement of electrodes 24, thereby creating poor electrode-to-tissue contact. Further, electrodes 24 may be positioned adjacent fibrous, dead or functionally refractory tissue. Electrodes 24 positioned adjacent fibrous, dead or functionally refractory tissue may not be able to sense changes in electrical potential because fibrous, dead or functionally refractory tissue may be incapable of depolarizing and/or responding to changes in electrical potential. Finally, far-field ventricular events and electrical line noise may distort measurement of tissue activity.

However, electrodes 24 that contact healthy, responsive cellular tissue may sense a change in the voltage potential of a propagating cellular activation wavefront. The change in voltage potential of cellular tissue may be sensed, collected and displayed as an electrogram. An electrogram may be a visual representation of the change in voltage potential of the cellular tissue over time. Additionally, it may be desirable to define a specific characteristic of an electrogram as a "fiducial" point of the electrical signal. For purposes of this disclosure, a fiducial point may be understood as a characteristic of an electrogram that can be utilized as an identifying characteristic of cellular activation. Fiducial points may correspond to the peak amplitude, change in slope, and/or deflection of the electrical signal. It is contemplated that fiducial points may include other characteristics of an electrogram or other signal used to generate diagnostic and/or processed output. Further, fiducial points may be identified manually by a clinician and/or automatically by processing system 32.

An electrogram representing a change in voltage potential over time may be defined as visually displaying the electrical signal in the "time domain." However, it is generally understood that any electrical signal has a corollary representation in the "frequency domain." Transforms (e.g. Fourier, Fast Fourier, Wavelet, Wigner-Ville) may be utilized to transform signals between the time (spatial) domain and frequency domain, as desired. Electrical signals also have a corollary representation in the analytic domain which can be obtained through transforms (e.g. Hilbert transform).

Further, in a normal functioning heart, electrical discharge of the myocardial cells may occur in a systematic, linear fashion. Therefore, detection of non-linear propagation of the cellular excitation wavefront may be indicative of cellular firing in an abnormal fashion. For example, cellular firing in a rotating pattern may indicate the presence of dominant rotors and/or divergent activation patterns. Further, because the presence of the abnormal cellular firing may occur over localized target tissue regions, it is possible that electrical activity may change form, strength or direction when propagating around, within, among or adjacent to diseased or abnormal cellular tissue. Identification of these localized areas of diseased or abnormal tissue may provide a user with a location for which to perform a therapeutic and/or diagnostic procedure. For example, identification of an area including reentrant or rotor currents may be indicative of an area of diseased or abnormal cellular tissue. The diseased or abnormal cellular tissue may be targeted for an ablative procedure. Various processed outputs, such as those described above, may be used to identify areas of circular, adherent, rotor or other abnormal cellular excitation wavefront propagation.

Figure 4:
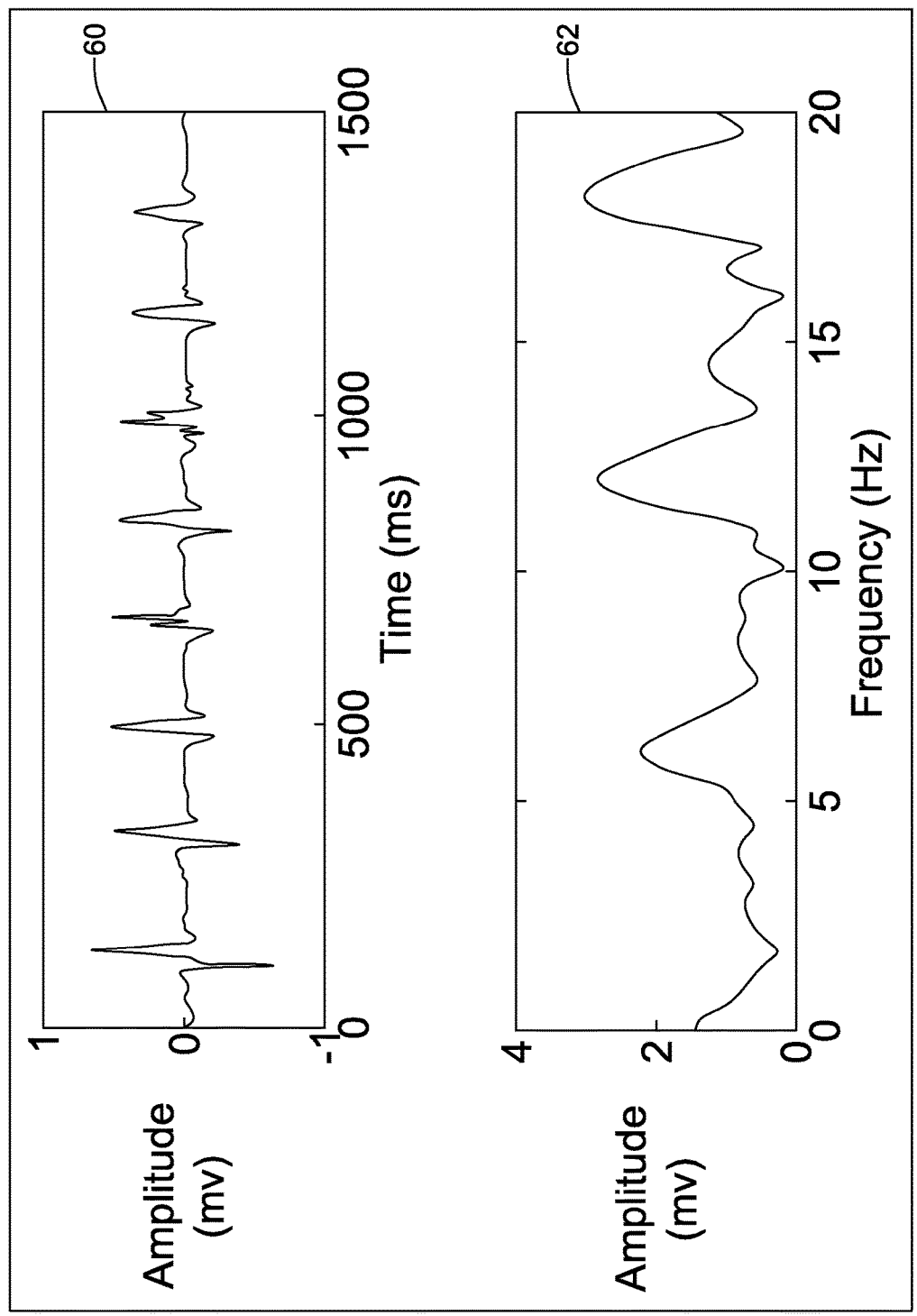
FIG. 4 is an illustration of an example electrogram signal in the time domain and a corresponding frequency representation in the frequency domain.

In at least some embodiments, the process of generating processed output may begin by collecting signals from one or more of sixty-four electrodes 24 on structure 20. As stated above, the sensed signals may be collected and displayed in the time domain. However, in at least one embodiment, signals displayed in the time domain may be transformed into the frequency domain to further generate processed output. As stated above, transforms such as the Fourier Transform, Fast Fourier Transform, or any other transform that produces frequency and power information for a signal may be utilized to transform signals between the time and frequency domains. FIG. 4 illustrates an example electrogram signal in the time domain 60 along with its corresponding frequency representation in the frequency domain 62.

After transforming the signal into the frequency domain, processing system 32 may construct, determine or calculate a composite signal or characteristic (e.g. frequency) common to one or more of the signals collected from the sixty-four electrodes 24 on structure 20. The composite signal may be constructed, determined or calculated by performing one or more mathematical, statistical or computational operations involving one or more of the signals collected from the sixty-four electrodes 24 on structure 20. For example, the composite signal may be determined by calculating the median amplitude and/or power value at each frequency for one or more of the signals collected from the sixty-four electrodes 24 on structure 20. FIG. 5c illustrates a composite signal 66 derived from contributing signals 68 and 70, shown in FIGS. 5a and 5b, respectively. FIG. 5c may illustrate a composite signal created by calculating the median power value for each frequency across signals 68 and 70. It should be understood that processing system 32 may incorporate sensed data values from one or more of the collected signals from one or more of the sixty-four electrodes 24 on structure 20. Further, calculating the statistical median for all frequencies across one or more signals is one of numerous possible methodologies processing system 32 may utilize to construct, determine or calculate a composite signal. For example, processing system 32 may utilize the mean, median, mode or any other mathematical, statistical or computational operation to construct, determine or calculate a composite signal.

Figure 6:
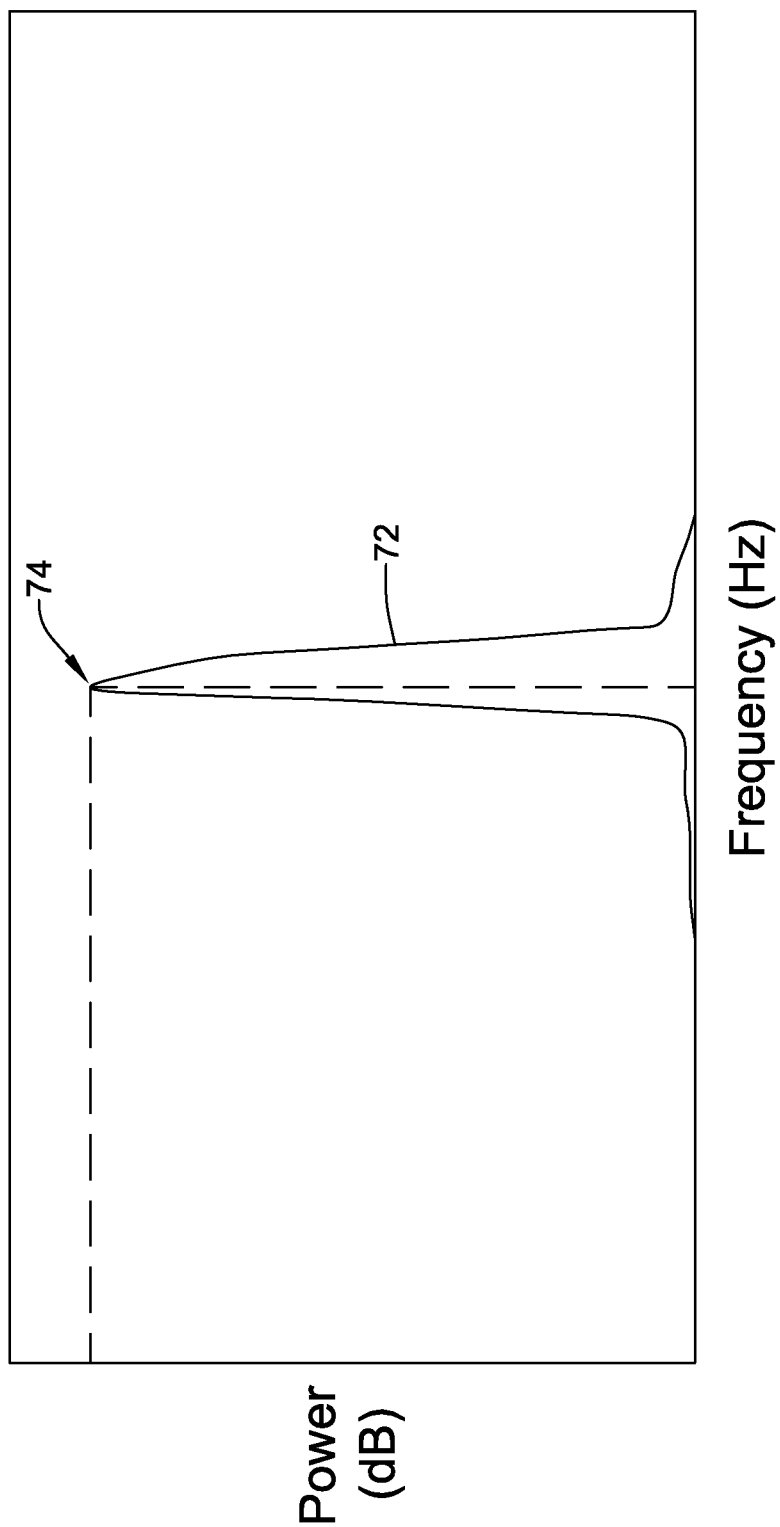
FIG. 6 is an illustration of an example composite frequency spectrum and its maximum power value.

Additionally, processing system 32 may determine a "characteristic frequency" from a generated composite signal. For example, after calculating the median power value for each frequency across collected signals, processing system 32 may determine the frequency at which the maximum power value occurs. The frequency at which the maximum power value occurs may represent the "median dominant frequency" of one or more collected signals contributing to the composite signal. This median dominant frequency may be considered the "characteristic frequency" of the collected signals. FIG. 6, for example, illustrates an example composite signal 72 and the frequency corresponding to its maximum power value 74.

As stated above, processing system 32 may utilize the mean, median, mode or any other mathematical, statistical or computational operation to construct, determine or calculate a composite signal. Additionally, the characteristic frequency may represent the median dominant, mean dominant frequency, mode dominant frequency or any other dominant or characteristic frequency derived from a variety of computational operations. Further, it should be understood that processing system 32 may not have to calculate a composite signal in order to generate, determine, select or derive a characteristic frequency. Rather, it may be possible for processing system 32 to determine a unique composite characteristic by analyzing the data collected from one or more of the signals collected from the sixty-four electrodes 24 on structure 20 independently of determining a composite signal.

Additionally, processing system 32 may select a range of frequencies for which data is utilized from one or more of the signals collected from the sixty-four electrodes 24 on structure 20. For example, a frequency range of 3-7 Hz has been shown (empirically) to be a frequency range in which abnormal cardiac electrical activity occurs. For example, atrial fibrillation may occur predominantly in the frequency range of 3-7 Hz. It is contemplated that other abnormal atrial events may also occur within this frequency range.

To that end, it may be desirable to filter and exclude collected electrical signal data outside of the 3-7 Hz frequency range. This may be accomplished by utilizing a bandpass filter having a passing region between 3-7 Hz. In other embodiments, processing system 32 may determine a composite signal or characteristic frequency by determining a median, mean, mode or other signal characteristic for frequencies between 3-7 Hz for each collected signal, thereby eliminating the need for a filtering step. Additionally, it should be understood that the selected and/or filtered frequency range may be greater or less than 3-7 Hz (e.g. each limit could be modified by ±2-10 Hz). Selecting or ignoring data within a particular frequency range may improve the techniques and/or processed output of the embodiments disclosed herein.

Additionally, processing system 32 may determine a phase value associated with a characteristic of the collected electrical signals. For example, processing system 32 may determine a phase value correlated to a determined characteristic frequency for one or more of the signals collected from electrodes 24 on structure 20. Further, a phase value may be determined at the median dominant frequency for one or more of the signals collected from electrodes 24 on structure 20. Additionally, the Fourier transform may be used to determine the phase value for a particular collected signal at a given frequency. Therefore, the Fourier transform may be used to determine the phase value for one or more of the signals collected from electrodes 24 on structure 20 at a characteristic frequency (e.g. the median dominant frequency).

In addition, processing system 32 may generate an alternate signal associated and/or correlated to each of the signals collected from electrodes 24 on structure 20. An alternate signal corresponding to each collected signal may include related and important features of the collected signal In the examples that follow, alternate signals may be described as sinusoids. However, it is contemplated that any of examples and/or embodiments that describe an alternate signal as a sinusoid may also be described by its analytic representation. For example, the analytic representation of a signal may be understood as a complex representation of the signal with no negative frequency components. The phase of the signal at each time point can be readily obtained from this analytic representation by comparing its real component with this imaginary component at each time point. The analytic signal may take the shape of a "sawtooth" wave pattern. The analytic signal representation may be obtained through the Hilbert transform. Further, it is contemplated that an alternate signal may be a signal other than a sinusoid and/or its analytic representation.

Additionally, it should be understood that an alternate signal correlated to a signal collected from electrodes 24 may contain characteristics related to the composite signal, composite characteristic and/or a dominant frequency of one or more of the collected signals. For example, the alternate signal may have a dominant frequency that is equal to the dominant frequency of the composite signal, composite characteristic and/or a dominant frequency of one or more of the collected signals from electrodes 24. In embodiments where the alternate signal is a sinusoid, the sinusoid may have a frequency equal to the dominant frequency of the composite signal, composite characteristic and/or a dominant frequency of one or more of the collected signals from electrodes 24. Further, alternate signals may contain additional information, such as amplitude, that reflect voltage values of one or more signals collected by electrodes 24. In addition, an alternate signal may display a consistent or repeated pattern that aligns with a collected signal (that may not display a uniform or consistent pattern over time). For example, an alternate sinusoid signal (displaying a uniform oscillation over a time period) may be correlated to an original (e.g. unipolar) signal whose amplitude and frequency varies significantly over the same time period. It should be understood that a time period described in the examples above may include and/or span N beats of an arrhythmic cardiac event (e.g. atrial fibrillation).

Figure 7A:
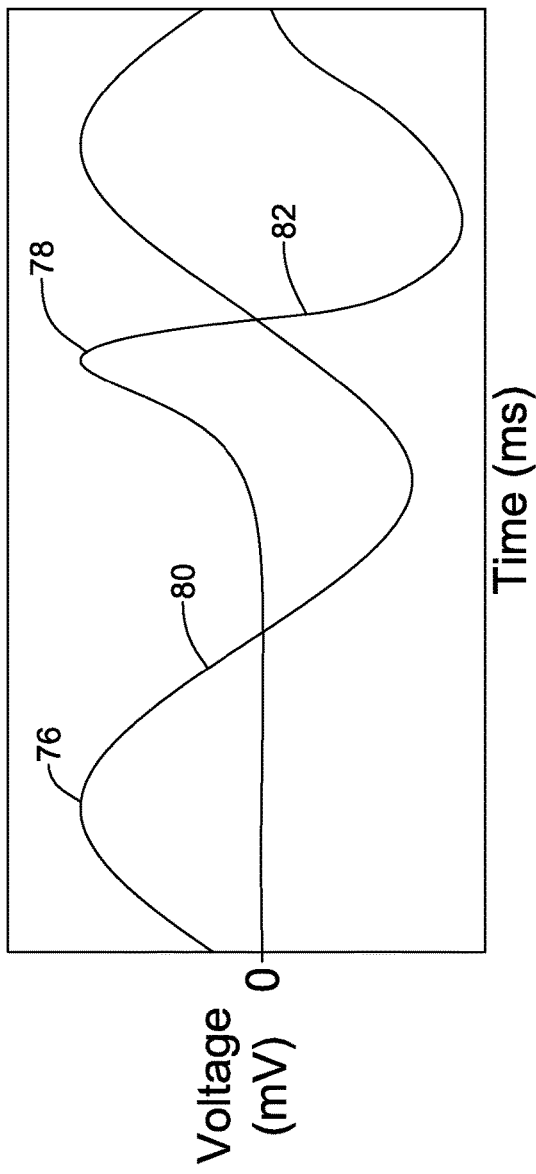
FIGS. 7A-7B are illustrations of example electrograms overlaid by a sinusoid signal.
Figure 7B:
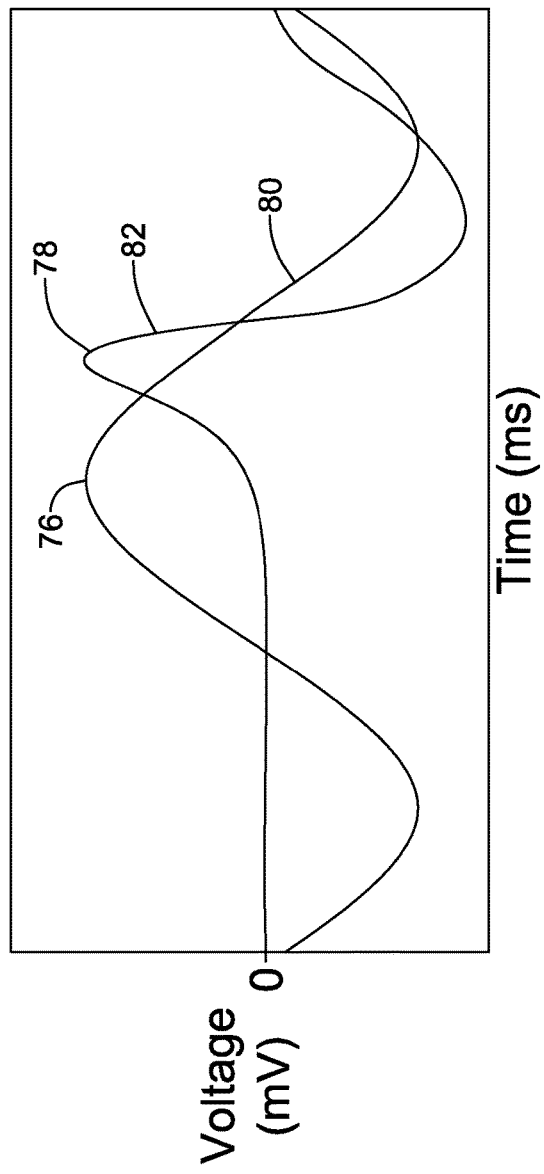

Additionally, to better utilize information derived from alternate signals, it may be desirable to align one or more alternate signals with one or more corresponding original, collected signals. The phase value derived from the frequency spectrum of a collected signal may be utilized to adjust, shift and/or correlate an alternate signal to its original (e.g. unipolar) signal. For example, alternate signals that are sinusoids may be assigned a phase value derived from their corresponding collected (e.g. unipolar) signal. The phase value may be used to modify or better align the alternate signal with the collected signal. Adjustment and/or modification of an alternate signal using the phase value may provide a more accurate estimation of important diagnostic information associated with the collected signals. For example, FIG. 7a illustrates original signal 78 overlaid by its unshifted alternate sinusoid signal 76. In FIG. 7a, the maximum negative derivative 82 of original signal 78 does not align with downstroke 80 of sinusoid 76. However, as shown in FIG. 7b, shifting sinusoid 76 by a phase value may better align the downstroke 80 of sinusoid 76 with the maximum negative derivative of collected signal 78.

Figures 8A, 8B:
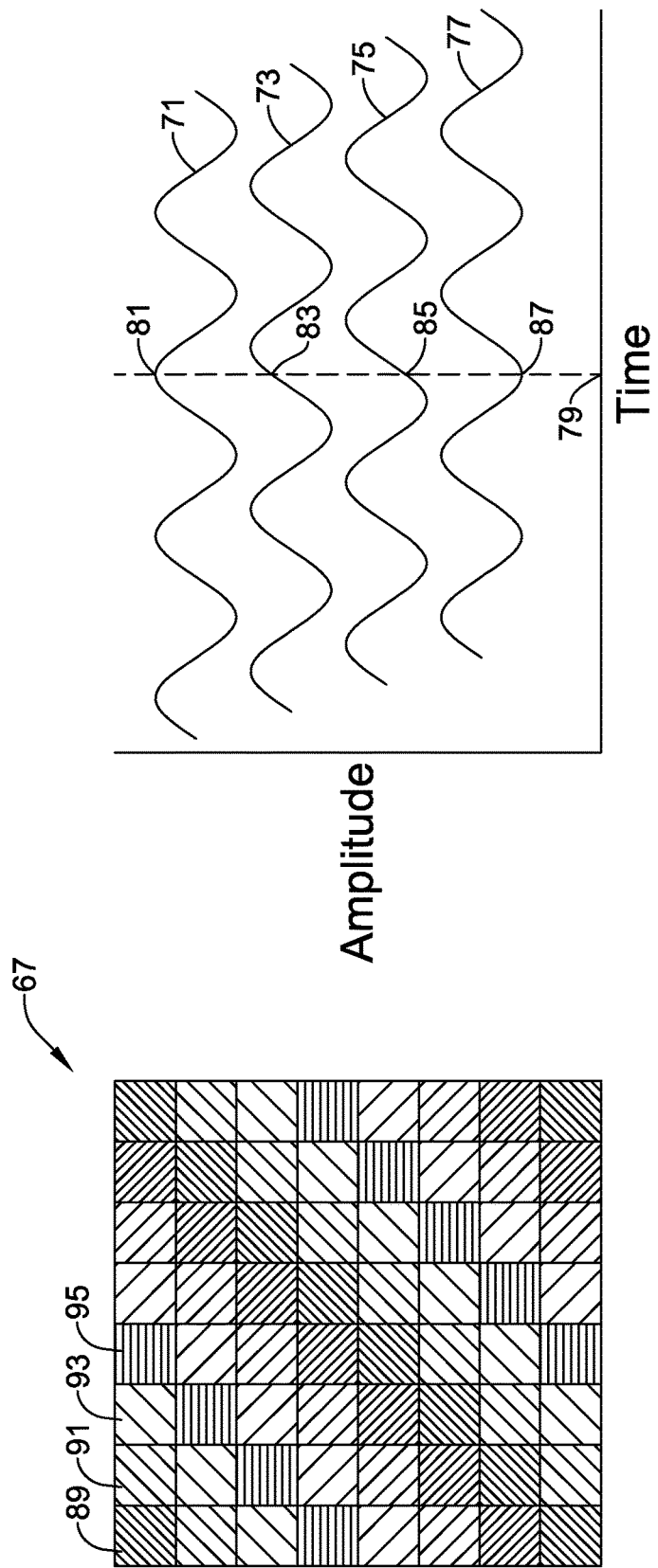
FIGS. 8A-8B are illustrations of example phase-shifted alternative signal sinusoids and corresponding dynamic displays.

Additionally, after one or more alternate signals have been phase-shifted to better align with the collected signals, it may be desirable to compare the amplitudes of one or more of the alternate (e.g., sinusoid, Hilbert representation, etc.) signals over time. For example, as stated above, depending on the characteristics of its corresponding original signal, the amplitude value of a given alternate signal may differ as compared to a second alternate signal derived from a second original signal. Further, the amplitude values (at a given time) may differ for one or more of the alternate signals derived from one or more of the signals collected from electrodes 24. For example, FIG. 8b shows an example "amplitude vs. time" plot of phase-shifted, alternate sinusoid signals 71, 73, 75 and 77. FIG. 8b illustrates that at time point 79, phase-shifted, alternate sinusoid signals 71, 73, 75 and 77 may have different amplitude values 81, 83, 85 and 87, respectively. Further, it is understood that the amplitude value of any one of signals 71, 73, 75 and 77 will change over a given time period.

To that end, it may be desirable to compare the amplitude values of one or more alternate signals over a given time period. Further, it may be desirable to display the numerical values of the amplitudes in a dynamic display. For example, it may be desirable to generate a "movie" or "dynamic display" comparing the amplitudes sensed by electrodes 24. FIG. 8a shows example dynamic display 67 displaying amplitude values (e.g., corresponding to amplitude values 81, 83, 85 and 87 of signals 71, 73, 75 and 77) in spaces 89, 91, 93 and 95. It can be appreciated that different numeric amplitude values may be represented by a color spectrum. For example, a given color (e.g. red) may represent amplitude values of 0-0.1, while a different color (e.g. orange) may represent amplitude values of 0.11-0.2, for example. FIG. 8a shows spaces 89, 91, 93 and 95 which correspond to amplitude values 81, 83, 85 and 87 of signals 71, 73, 75 and 77. Further, spaces 89, 91, 93 and 95 display different cross-hatch patterns as compared to one another. The different cross-hatch patterns may represent different colors as they relate to the specific amplitude values 81, 83, 85 and 87 of signals 71, 73, 75 and 77.

It is understood that over a given time period, the colors of spaces 89, 91, 93 and 95 will change as the amplitude values 81, 83, 85 and 87 of signals 71, 73, 75 and 77 change. Further, it should be understood that alternate signals 81, 83, 85 and 87 may correspond to four of sixty-four electrodes 24 on structure 20. It should be further understood that FIGS. 8a and 8b are only illustrative, and therefore, may represent any number of the sixty-four electrodes 24 on structure 20. Over time, the continual changing of colors may be displayed, or "played" as a dynamic display or movie representing the sixty-four electrodes 24 on structure 20. This movie or dynamic display may provide a medium that allows better visualization of the cellular wavefront propagation and/or the focal impulse of cellular activity over N beats of an arrhythmic cardiac event (e.g. atrial fibrillation).

Utilizing the amplitude values derived from alternate sinusoid signals (or analytic representation) may provide a "smoothing effect" to the dynamic display as compared to utilizing amplitude values derived directly from original, collected signals. Further, application of the Hilbert transform to the alternate sinusoid signals may result in a dynamic display that is clearer than displays generated by other alternative signals.

In addition to generating a dynamic display, it may be desirable to generate a static display from fiducial points (e.g. activation times) derived from alternate signals. A fiducial point may be understood as a characteristic of an electrogram that can be utilized to identify cellular activation (e.g. cellular depolarization). For example, it is contemplated that fiducial points may include any characteristic of a sinusoid signal during its phase length. For example, activation times may be correlated to peak amplitude, phase, maximum negative derivative or zero-crossing. These are just examples.

Further, it may be desirable to display an activation map related to fiducial points derived from alternative sinusoid signals. The activation map may represent the relative activation times of electrodes 24 for one cycle in a multi-cycle cardiac event. In contrast to the dynamic display, an activation map may need to be "refreshed" for each cycle in a multi-cycle cardiac event.

Figure 10:
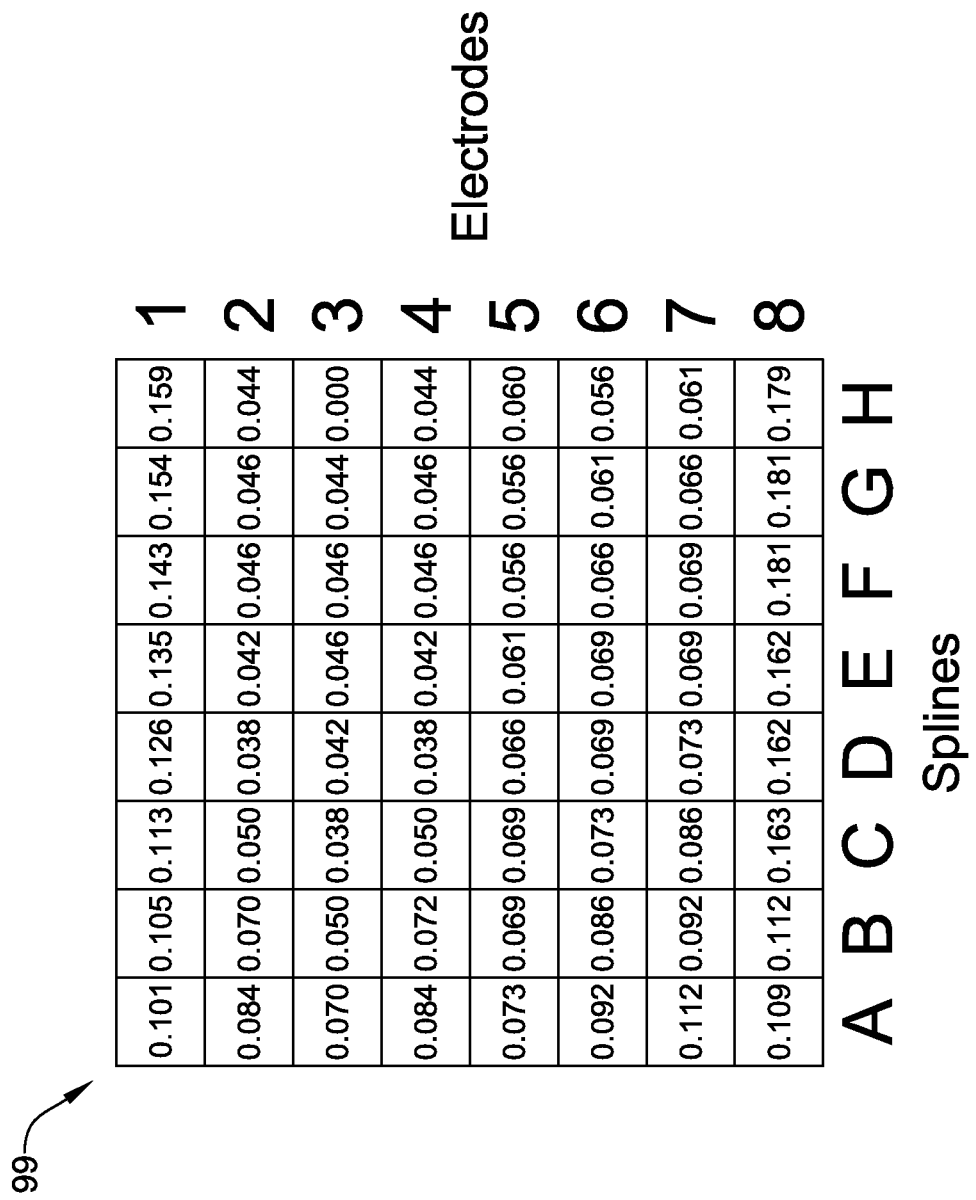
FIG. 10 is an illustration of an example activation map displaying activation times.

For the purposes of this disclosure, the time at which a fiducial point occurs relative to a reference time (the reference time may be the time a reference electrode senses a cellular activation and, for convenience, is set to 0) corresponds to the activation time for a given electrode. The various times that are determined as the activation times for each of the alternate signals may be compared, categorized and/or displayed. The activation times may be displayed in an activation map 99 as illustrated in FIG. 10.

Alternatively, it may be desirable to determine the "true" activation times of the original, collected signals. However, selecting activation times from the original signal characteristics may prove challenging. For example, automated activation time selection on original (e.g. unipolar) signals may result in the mislabeling of fiducial points, thereby leading to faulty interpolation of multi-electrode array data. Further, increased processing power may be required to implement methodologies and algorithms associated with automated selection. Therefore, it may be desirable to utilize a methodology which more efficiently and/or accurately determines the "true" activation times of original, sensed signals.

In some embodiments, sensing the "true" activation time may be accomplished by aligning an "estimated" fiducial point on an alternate signal with that of the "true" activation time of the original signal. For example, it may desirable to determine true activation times by comparing and/or relating signal characteristics of the original and alternate signals. For example, processing system 32 may determine the time at which the zero-crossing on the alternate signal occurs. Having determined the time at which zero-crossing on the alternate signal occurs, processing system 32 may compare that time with the time at which the maximum negative derivative on the original signal occurs. If the time at which the original signal characteristic occurs is sufficiently close to the time at which the alternate signal characteristic occurs, processing system 32 may assign the time at which the original signal characteristic (e.g. maximum negative derivative) occurs as the activation time of the original signal. In other words, in order to provide increased confidence that a given signal characteristic (e.g. maximum negative derivative) accurately represents the true activation time of cellular tissue, processing system may create a "window" or "tolerance window" of time around the time at which the alternate signal characteristic occurs and determine whether a given signal characteristic on the original signal falls within that "window" of time.

Figure 9:
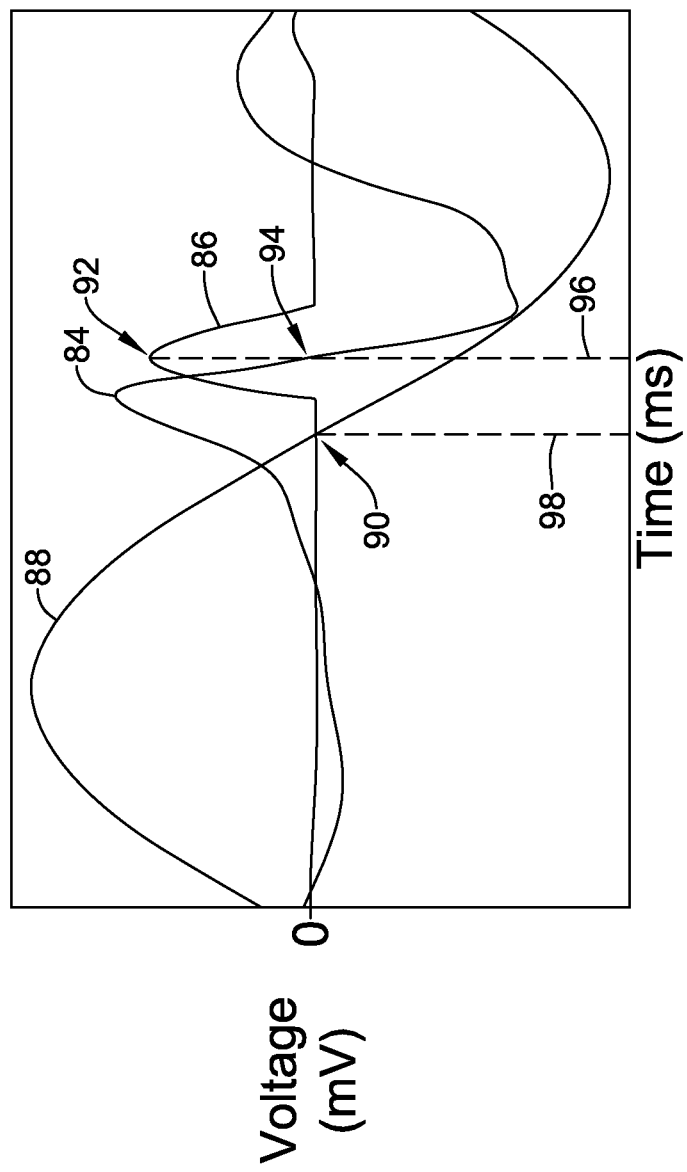
FIG. 9 is an illustration of an example alternate sinusoid signal overlaid an original signal.

FIG. 9 illustrates an example schematic of the "windowing" methodology described above. FIG. 9 displays electrogram 84 overlaid with a plot of its negative derivative 86 and alternate sinusoid signal 88. As illustrated in FIG. 9, electrogram 84 has a maximum negative derivative value 92 that correlates with the maximum negative slope 94 of electrogram 84 at time point 96. While not illustrated in FIG. 9, processing system 32 may detect other time values at which electrogram 84 displays a downward slope and corresponding negative derivative. In some embodiments, processing system may select the time point of the maximum negative derivative of the electrogram as the activation time of the sensed electrogram signal.

Additionally, processing system 32 may select the time point of the maximum negative derivative of the electrogram as the activation time of the electrogram signal 84 only if the time point lies within a predetermined "window" of time as compared to a zero-crossing point of an alternate signal. For example, FIG. 9 illustrates zero-crossing point 90 of alternate sinusoid signal 88 occurring at example time point 98. Processing system 32 may compare time point 96 (corresponding to the maximum negative derivative value 92) with time point 98 (corresponding to the zero-crossing point of alternate signal 88). If time point 96 is within the predetermined "window" of time, processing system 32 may select time point 96 as the activation time of electrogram signal 84. It is contemplated that the "window" of time value may be user determined and/or pre-programmed into a selection algorithm of processing system 32, such as "% of cycle length" or a "multiplier of cycle length."

Additionally, it is contemplated that processing system 32 may, over time, adjust the frequency and phase of the alternate signal by comparing the selected activation times on the original (e.g. electrogram) signal with the corresponding zero-crossing points (or other fiducial point) on the alternate signal. For example, processing system may compare the original signal and alternate signal time points over the near-term historical data (e.g. last N beats of a cardiac cycle). Further, a constant offset or difference between the selected activation times and corresponding zero-crossing on the alternate signal over the last N beats indicates that the phase of the alternate signal is off and may be adjusted to mitigate the constant offset. Additionally, an offset or difference that systematically increases (or decreases) over the last N beats, for example, may indicate that the frequency of the alternate signal is higher (or lower) than optimal and may be adjusted to mitigate the slope of the difference over the last N beats. A regression may be performed over the difference between the selected activation times and corresponding zero-crossing on the alternate signal over the last N beats as a function of beat number. Further, the resultant slope and intercept could be used to update/adjust the frequency and phase of the alternate signal. The process can be repeated periodically.

In addition, processing system 32 may utilize "threshold" values for which signal characteristics must meet in order for processing system 32 to include them in an algorithm, process or calculation of processed output (e.g. activation times). For example, processing system 32 may use a "maximum derivative magnitude" as a threshold value for the maximum negative derivative calculation. Additionally, if processing system 32 fails to identify signal characteristics that meet predetermined threshold values, processing system 32 may use fiducial time points as the default assignment of processed output (e.g. activation times). For example, if the a signal characteristic on an original signal (e.g. maximum negative derivative) does not fall within a chosen "window of time" as described above or does not meet a maximum derivative threshold, the signal characteristic on the alternate signal (e.g. zero-crossing) may be selected as the processed output (e.g. activation time).

While the above examples identify the original and the alternate signal characteristics as the maximum negative derivative and the zero-crossing, respectively, it should be understood that signal characteristics may be any characteristic other than, or in addition to, those identified above.

While the "windowing" methodology described above may be useful in selecting and/or determining true activation times, other methods are contemplated. For example, processing system 32 may incorporate a statistical-based methodology and/or algorithm to predict, refine and select true activation times from original, sensed signals. In one example methodology, processing system 32 may incorporate known or sensed data (e.g., activation times and/or electrograms) to generate the probability of the occurrence of future activation times. As data is collected, processing system 32 may adjust the statistical algorithm based on previously collected data. Selection of true activation points of future activation wavefronts may then be based on a probability distribution calculated by the past activation events. Furthermore, the statistical-based algorithm may attempt to introduce and/or model sources of uncertainty within the statistical model. In some embodiments, utilizing a statistical algorithm may require processing system 32 to first generate an "activation" signal for each of the original signals from one or more of electrodes 24 on structure 20 and, second, use the activation signals to estimate an overall cycle length of the arrhythmic cardiac event.

Generating an activation signal for each electrode location on a sensing device may include sensing and converting the original signals to modified signal. An activation signal for each electrode location may incorporate the data sensed by the individual electrode location over a period of time. For example, an activation signal may include data sensed over N beats of an arrhythmic cardiac event (e.g. atrial fibrillation). Further, modifying the original signals may include selecting important signal information while eliminating and/or filtering less-desirable information. For example, original, sensed signals may include three primary components: far-field activation, local activation and power line noise. In contrast, activation signals may eliminate a portion or all of these three primary components.

To that end, power line noise may be reduced and/or removed by utilizing an adaptive filter. Additionally, a spatial filter may be utilized to remove far-field signals. Far field signals may be present in electrodes 24 which are not in contact with cardiac tissue. Therefore, a spatial filter may use a first-order polynomial model based on the approximate shape of the sensing device (e.g. Constellation catheter). Alternatively, many of the same benefits to using an adaptive filter to remove power line noise and a spatial filter to remove far-field signals may be achieved by subtracting the mean (or a weighted mean) of the measured signals.

The next steps in generating activation signals may include: calculating the first-difference of each measurement, setting the positive values to zero (thereby discarding positive deflections), applying a low-pass filter to smooth out multiple deflections and inverting the activation signal such that it is positive-valued.

As stated above, after generating an activation signal for each electrode location, the next step in a statistical-based methodology is utilizing the activation signals to estimate the overall cycle length of the arrhythmic cardiac event. For example, the steps may include computing the power spectrum (e.g. by utilizing Welch's method) of each activation signal, adding a noise floor, taking the FFT of the log power spectrum to get the cepstrum, averaging the cepstra of the electrodes, and selectively choosing peak values to derive the cycle length.

After determining both the activation signal and estimating the cycle length, the next step in utilizing a statistical-based methodology to select activation times for each electrode may include utilizing an "iterative" statistical algorithm. For example, the methodology may include using Bayes method to iteratively refine future activation time data based on probability distributions of past activation times.

Figure 11A:
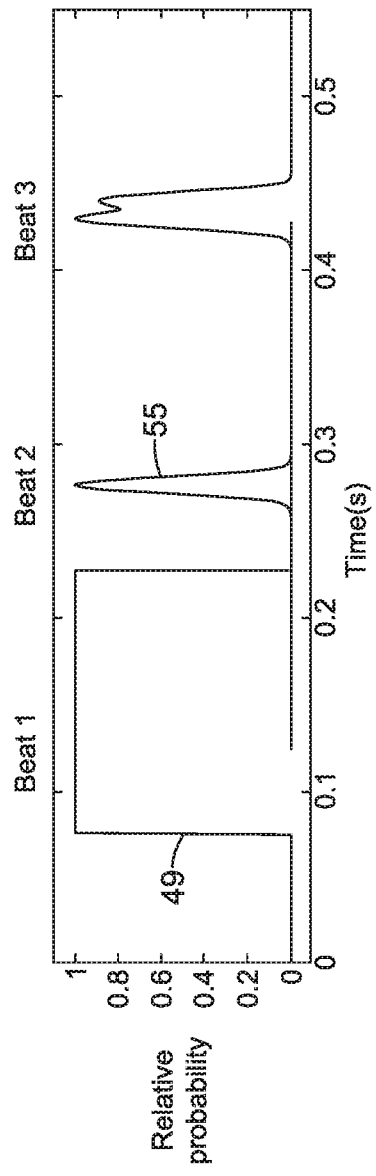
FIGS. 11A-11C are illustrations of example activation signals overlaid by probability distributions.
Figure 11B:
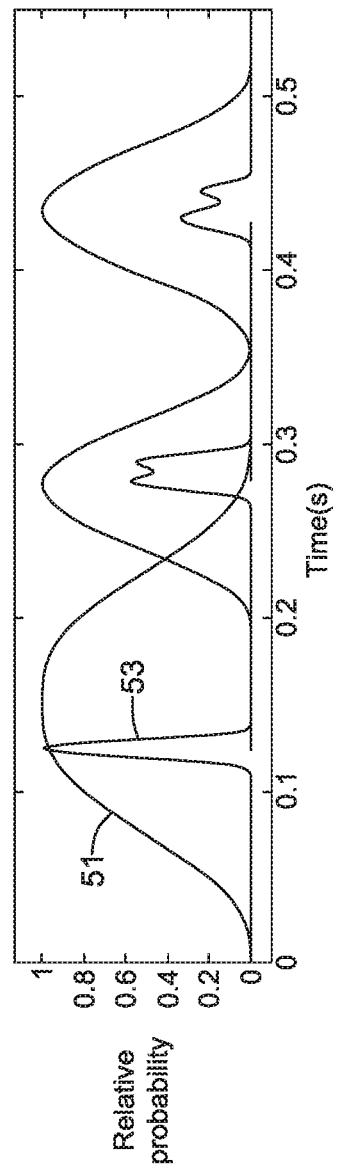
Figure 11C:
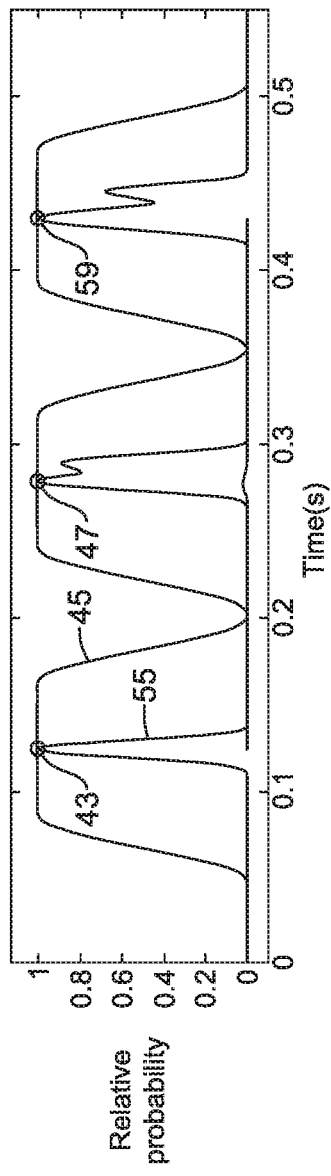

FIGS. 11a-11c illustrate an example statistical algorithm using the activation signal and cycle length (described above) along with Bayes method to determine true activation times of example cardiac wavefronts. FIGS. 11a, 11b and 11c represent the steps performed by the statistical algorithm spanning three beats of a cardiac cycle. The first step in the statistical algorithm may include utilizing a pre-selected, initialization probability function as a first predication of the probability of cellular activation times. In FIG. 11a, initialization probability function 49 is illustrated under the column titled "Beat 1." The next step in the statistical algorithm may include smoothing initialization probability function 49 with a low pass filter. This step may result in a Gaussian-shaped smoothed probability function 51, which is illustrated under the column titled "Beat 1" of FIG. 11b. It should be understood that this "smoothing" step may not be necessary for the first initialization step. However, the "smoothing" step models the uncertainty in predicting subsequent activation times. In some embodiments the smoothed probability function 51 may be referred to as the a priori probability function. Further, while examples herein disclose initialization probability function 49 and smoothed probability function 51 as a box and Gaussian shape, respectively, it is contemplated that a wide variety of probability of distribution curve shapes may be utilized in any of the steps disclosed herein.

After generating smoothed probability function 51, processing system 32 may multiply the activation signal 53 by the initialization probability function 49 to generate a posteriori probability distribution 55. A posterior probability distribution 55 is illustrated under the "Beat 1" column of FIG. 11c. After generating a posterior probability distribution 55, the greatest peak 43 of a posterior probability distribution 55 is selected as the true activation time for beat 1 of the cardiac cycle.

After selecting peak 43, processing system 32 may perform a regularization step. The regularization step may include multiplying fixed window 45 by a posterior probability distribution 55. In some embodiments, the regularization step may reduce the effects of adjacent beats, which may otherwise accumulate over subsequent steps of the statistical algorithm.

Lastly, a posterior probability 55 is time shifted one cardiac cycle (the steps of generation having been disclosed above) and is used as the initialization probability distribution 55 of the subsequent beat in the cardiac cycle. The subsequent beat is illustrated in FIGS. 11a-11c under the "Beat 2" column. At this point, the statistical algorithm repeats itself, starting with smoothing the initialization probability distribution 55. As the process repeats itself, it selects true activation times for each beat. However, as stated above, the activation times chosen for a given beat are influenced by prior data and probability distributions derived from previous beats. In FIG. 11c, for example, activation time 47 has been influenced by prior data corresponding to beat 1. Similarly, activation time 59 has been influenced by prior data corresponding to both beat 1 and beat 2 (as beat 2 has been influenced by beat 1). In both cases, activation times 47 and 59 have been chosen as the greatest peak on the posterior distributions for beats 2 & 3, respectively.

After activation times (and/or corresponding fiducial points) have been identified, it may be desirable to display one or more processed outputs. For example, in some embodiments in may be desirable to compare and categorize the derived activation times of the collected signals. As described above, it may be desirable to display relative activation times in an activation map. An example activation map 99 is shown in FIG. 10. FIG. 10 displays activation times corresponding to the sixty-four electrodes 24 on structure 20. However, while the numerical values may be useful, in practice the data may utilize a color scheme, patterns, or the like to convey the information.

It should be understood that processing system 32 may selectively eliminate some of the collected signals before performing the techniques and/or embodiments disclosed herein. For example, it may be beneficial to eliminate signals collected by electrodes that are not in electrical contact, or in poor electrical contact, with excitable cellular tissue of the heart. Such signals may not provide useful information and can skew results of the above described techniques. Further, processing system 32 may eliminate collected signals that do not cross a threshold power level and/or may eliminate collected signals that display a threshold amount of noise.

Alternatively, instead of eliminating collected signals that are not providing useful information, processing system 32 may instead interpolate the value of any signal which is not otherwise providing desirable information. Processing system 32 may utilize the interpolated data (e.g. signal data) to better calculate, determine or generate useful processed data and/or smooth, refine, or present processed data in a more desirable manner.

In at least some of the embodiments described above the disclosed methods assume analysis of sensed, collected, measured and transmitted electrical cellular data occurring during a single heartbeat and/or cardiac pulse. However, it is contemplated that any of the disclosed methods may be implemented across multiple beats or cardiac pacing time intervals. Further, data collected over multiple heart beats may be analyzed using statistical methodologies and applied to the disclosed methods. For example, activation times may be collected over a series of heart beats and/or pulses. A statistical distribution of the collected activation times may be calculated, analyzed and incorporated into disclosed methods.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A method of using a system to map electrical activity of a heart, the system comprising (1) a mapping probe having a plurality of electrodes disposed at a distal end of the mapping probe, (2) a processing system, wherein each electrode of the plurality of electrodes is electrically coupled to the processing system, and (3) a display device coupled to the processing system, the method comprising:
   sensing a plurality of signals with the plurality of electrodes positioned within the heart;
   determining, by the processing system, a dominant frequency of the plurality of signals;
   generating, by the processing system, an alternate signal for each of the plurality of signals corresponding to the dominant frequency, wherein each of the alternate signals has a phase-shift corresponding to one of the plurality of signals;
   determining, by the processing system, an activation time corresponding to each of the plurality of signals, wherein determining the activation time corresponding to each of the plurality of signals comprises, for a first signal of the plurality of signals and a corresponding first alternate signal:
      determining a first time, the first time comprising a time at which a characteristic of the alternate signal occurs;
      creating a window of time around the first time;
      determining a second time, the second time comprising a time at which a characteristic of the first signal occurs;
      determining that the second time occurs within the window of time; and
      selecting, in response to determining that the second time occurs within the window of time, the second time as the activation time corresponding to the first signal;
   generating, based on the determined activation times, an activation map; and
   displaying, by the processing system and on the display device, the activation map.

2. The method of claim 1, wherein determining a dominant frequency comprises:
   processing each of the plurality of signals using a Fourier Transform;
   generating a composite signal based on the processed plurality of signals;
   identifying the frequency with the maximum power in the composite signal.

3. The method of claim 2, further comprising band-pass filtering each of the processed plurality of signals.

4. The method of claim 3, wherein the band-pass filtering comprises passing data in the 3 to 7 Hz band for each of the processed plurality of signals.

5. The method of claim 2, wherein generating the composite signal based on the processed plurality of signals comprises:
   generating the composite signal with a value at each frequency that is one of a median value, a mean value, or a mode value of the processed plurality of signals at each frequency.

6. The method of claim 5, wherein the phase-shift of the alternate signals are based on the composite signal.

7. The method of claim 6, wherein each alternate signal is a sinusoid.

8. The method of claim 7, wherein each alternate signal is an analytic representation of a sinusoid.

9. The method of claim 8, wherein the analytic representation is generated by a Hilbert transform.

10. The method of claim 8, wherein the analytic representation is a sawtooth.

11. The method of claim 7, further comprising determining a fiducial point on each alternate signal, and wherein the fiducial point on each alternate signal is one of the following:
    a point with a maximum negative derivative;
    a point of zero-crossing; and
    a point at phase $\pi/2$.

12. The method of claim 11, further comprising determining an activation time for each of the plurality of signals based on the identified fiducial points, generating an activation map based on the determined activation times for each of the plurality of signals, and displaying the activation map.

13. A system for mapping the electrical activity of the heart, the system comprising:
    a catheter shaft;
    a plurality of electrodes coupled to the catheter shaft, the plurality of electrodes configured to sense a plurality of cardiac signals; and
    a processor coupled to the catheter shaft, wherein the processor is configured to:
       receive the plurality of signals sensed by the plurality of electrodes;
       determine a dominant frequency of the plurality of signals;
       generate an alternate signal for each of the plurality of signals corresponding to the dominant frequency, wherein each of the alternate signals has a phase-shift corresponding to one of the plurality of signals;
       determine an activation time corresponding to each of the plurality of signals, wherein to determine the activation time corresponding to each of the plurality of signals comprises, for a first signal of the plurality of signals and a corresponding first alternate signal:
          determine a first time comprising a time at which a characteristic of the alternate signal occurs;
          create a window of time around the first time;
          determine a second time comprising a time at which a characteristic of the first signal occurs;
          determine that the second time occurs within the window of time; and
          select the second time as the activation time corresponding to the first signal in response to determining that the second time occurs within the window of time;

generate an activation map based on the determined activation times; and displaying the activation map.

14. The system of claim 13, wherein to determine a dominant frequency of the plurality of signals, the processor is further configured to:

transform each of the plurality of signals into the frequency domain;

generate a composite signal from each of the transformed plurality of signals; and identify the frequency that has the maximum power in the composite signal.

15. The system of claim 13, wherein each alternate signal is an analytic representation of a sinusoid.

16. The system of claim 15, wherein the analytic representation is a sawtooth.

* * * * *